United States Patent [19]

Sheth et al.

[11] Patent Number: 4,954,349
[45] Date of Patent: Sep. 4, 1990

[54] ORAL MAGNESIUM AND POTASSIUM COMPOSITIONS AND USE

[75] Inventors: Pravin B. Sheth, Netcong; Frederick J. Dechow, Summit, both of N.J.

[73] Assignee: Ciba-Geigy Corporation, Ardsley, N.Y.

[21] Appl. No.: 325,106

[22] Filed: Mar. 17, 1989

Related U.S. Application Data

[63] Continuation of Ser. No. 95,750, Sep. 11, 1987, abandoned.

[51] Int. Cl.$^5$ ................................................ A61K 9/36
[52] U.S. Cl. ...................... 424/461; 424/441; 424/464; 424/468; 424/470; 424/474; 424/475; 424/480
[58] Field of Search ............ 424/464, 470, 468, 475, 424/474, 461, 462, 441, 480, 494; 414/497

[56] References Cited

U.S. PATENT DOCUMENTS

| | | | |
|---|---|---|---|
| 2,478,182 | 8/1949 | Consolazio | 424/473 X |
| 3,538,214 | 11/1970 | Polli et al. | 424/473 X |
| 3,903,297 | 9/1975 | Robert | 514/573 X |
| 4,080,446 | 3/1978 | Leopold et al. | 514/161 |
| 4,104,370 | 8/1978 | Bloch | 424/153 |
| 4,348,378 | 9/1982 | Kosti | 424/49 X |
| 4,348,385 | 9/1982 | Gaffar et al. | 424/49 X |
| 4,572,833 | 2/1986 | Pedersen et al. | 424/470 X |

FOREIGN PATENT DOCUMENTS

| | | |
|---|---|---|
| 190512 | 10/1985 | Hungary . |
| 1356097 | 6/1974 | United Kingdom . |
| 1422193 | 1/1976 | United Kingdom . |

OTHER PUBLICATIONS

Derwent Abstract of Hungarian 190512 (T/035530A) Oct. (1985).
John W. Hollifield, M.D., American Journal of Medicine, 11/5/84, pp. 28-32.

*Primary Examiner*—Thurman K. Page
*Attorney, Agent, or Firm*—Irving M. Fishman

[57] ABSTRACT

Solid oral composition for the treatment or prophylaxis of potassium and magnesium deficiency in skeletal and cardiac muscle containing about 3 to about 50 milliequivalent bioavailable potassium, about 0.1 to about 25 milliequivalent bioavailable magnesium, and a milliequivalent ratio of potassium to magnesium between about 2:1 and about 14:1, where the potassium is in a controlled release form, and methods of treating or preventing potassium and magnesium deficiency by oral administration of such compositions.

9 Claims, No Drawings

ORAL MAGNESIUM AND POTASSIUM COMPOSITIONS AND USE

This application is a continuation of application Ser. No. 095,750, filed Sept. 11, 1987, now abandoned.

BACKGROUND OF THE INVENTION

The present invention relates to improved oral compositions for the treatment or prophylaxis of concurrent intracellular potassium and magnesium deficiencies in skeletal and cardiac muscle associated with gastrointestinal depletion or renal losses thereof, and the treatment of patients in need of the same.

A number of clinical conditions are associated with concurrent potassium and magnesium depletion in skeletal and cardiac muscle. Broadly, these include gastrointestinal depletion due to, for example, dietary deficiencies; malnutrition; malabsorption such as that occasioned by other electrolyte disturbances, especially hypocalcemia during infancy; diarrhea; primary hypomagnesia; intravenous therapy in the presence of extrarenal losses of magnesium and potassium; and the like; and to renal losses, especially renal losses occasioned by, for example, drug induced losses, including loop-blocking diuretics, gentamicin, cisplatin, ethanol, and the like; postobstructive diuresis; renal tubular acidosis or acute tubular necrosis; primary magnesium wasting due to intrinsic renal defects in magnesium reabsorption; Bartter's syndrome; hyperaldosteronism; and the like.

Clinical evidence of intracellular potassium and magnesium depletion as demonstrated by lymphocyte electrolyte analysis in patients with congestive heart failure has been shown, and magnesium sulfate has been described as administered either intravenously or intramuscularly to produce significant increases both lymphocyte magnesium and potassium levels. The role of magnesium deficiency in the pathogenesis of cardiovascular disease and arrhythmias, including digitalis-toxic arrhythmias and the use of magnesium to treat the same has also been reported.

It is known that extracellular and intracellular levels of sodium, calcium, potassium and magnesium differ greatly. Thus sodium and calcium concentrations are higher in extracellular compartments, while the concentration of potassium and magnesium are much higher within cells than without. Skeletal and cardiac muscle cells require adequate magnesium levels in order to maintain normal cell potassium. As a result, cellular magnesium deficiency results in decreased cell potassium and concurrent intracellular potassium and magnesium deficiencies in skeletal and cardiac muscle results in greater loss of cell potassium than would occur with potassium deficiency alone. Consequently, uncorrected coexisting magnesium cell depletion retards the repletion of cell potassium. For a comprehensive review of the role of magnesium in cell potassium deficiency, see for example, P. K. Whelton et al., Potassium in Cardiovascular and Renal Medicine, pages 23-35 (1986), Marcell Decker, Inc.

It is an object of the present invention to provide an improved oral solid dose form composition for the treatment or prophylaxis of concurrent intracellular potassium and magnesium deficiencies in skeletal and cardiac muscle associated with gastrointestinal depletion or renal losses thereof, wherein the composition contains, per unit dose, between about 3 and about 50 milliequivalents of potassium in the form of a bioavailable pharmaceutically acceptable salt thereof, between about 0.1 and about 25 milliequivalents of magnesium in the form of a bioavailable pharmaceutically acceptable salt thereof, in a milliequivalent ratio of potassium to magnesium of between about 2:1 and about 14:1, and wherein the potassium salt is subject to controlled release such that, upon oral administration, bioavailable potassium is released into the gastrointestinal tract at a rate sufficiently low so as to minimize potassium induced local gastrointestinal irritation.

It is a further object of the present invention to provide a method of treating or preventing intracellular potassium and magnesium deficiencies in skeletal and cardiac muscle associated with gastrointestinal depletion or renal losses thereof in a patent in need of the same, by orally administering to such patient an effective repleting amount of such composition.

These and other objects of the present invention are apparent from the following detailed disclosures.

DETAILED DESCRIPTION OF THE INVENTION

One embodiment of the present invention relates to a solid oral dose form composition for the treatment or prophylaxis of concurrent intracellular potassium and magnesium deficiency in skeletal and cardiac muscle associated with gastrointestinal depletion or renal losses thereof, wherein the composition comprises, per unit dose (a) between about 3 and about 50 milliequivalents of potassium in the form of a bioavailable pharmaceutically acceptable salt thereof;

(b) between about 0.1 and about 25 milliequivalents of magnesium in the form of a bioavailable pharmaceutically acceptable salt thereof;

(c) wherein the milliequivalent ratio of bioavailable potassium to bioavailable magnesium in said composition is between about 2:1 and about 14:1; and (d) wherein the bioavailable potassium is present in said composition in a controlled release form, such that, upon oral administration, the bioavailable potassium is released into the gastrointestinal tract at a rate sufficiently low so as to minimize potassium induced local gastrointestinal irritation.

Suitable bioavailable potassium salts are well known, per se, in the art and include conventional pharmaceutically acceptable organic and inorganic dietary supplement salts of potassium such as potassium citrate, potassium acetate, potassium bicarbonate, and especially potassium chloride.

Similarly, bioavailable magnesium salts are well known, per se, in the art and include conventional pharmaceutically acceptable organic and inorganic dietary supplement salts of magnesium such as magnesium oxide, magnesium phosphate, magnesium diphosphate, magnesium carbonate, magnesium aspartate, magnesium aspartate hydrochloride, magnesium chloride and the hydrates thereof, and the like.

The bioavailable potassium is in a controlled release form wherein, upon ingestion, the potassium is released into the gastrointestinal tract over a prolonged period of time in order to substantially minimize a high localized concentration of potassium ion in the region of the composition. Such high, localized concentration of potassium ions have been reported in the dissolution of non-controlled release forms of potassium supplements to produce gastrointestinal irritation, including stenotic and/or ulcerative lesions, gastrointestinal bleeding or perforation, or intestinal obstruction.

The composition may be in the form of conventional pharmaceutical solid unit dosage forms such as a tablet, capsule or sachet or the like, containing the potassium and magnesium components in the requisite ratio, wherein at least the potassium component is in the requisite controlled release form.

For example, the potassium may be present in the core of a tablet, or the like, or as one component of a layered tablet in a controlled release form. Thus, the potassium salt may be present in the core of a tablet wherein the core is surrounded by a water-insoluble semipermeable membrane wall containing an exit passageway to form an osmotically driven dispenser. The magnesium component may be present in admixture with the potassium component in the core, or alternatively a portion or preferably all of the magnesium salt may be contained in an overcoating or the like applied to the outer surface of the membrane, such that upon ingestion the magnesium salt containing coating disintegrates or dissolves thereby releasing bioavailable magnesium while activating the osmotic device, thereby releasing the potassium into the gastrointestinal tract in a controlled continuous manner.

Osmotically driven active agent devices suitable for the delivery of potassium salts are described, for example, in U.S. Pat. No. 4,016,880.

Alternatively, the potassium salt may be present in the core of a tablet or the like in which the core matrix has been coated with a dialytic film which serves as a membrane to allow gastrointestinal fluid to reach the core matrix and dissolve the potassium salt which is then released in a controlled continuous manner by leaching from the core matrix. The magnesium salt may be present as a component of the core and thereby leached out from the matrix with the potassium, or a portion or preferably all of the magnesium may be contained in an overcoating applied to the outer surface of the membrane as described in the preceding paragraph. Tablet core leaching devices suitable for the delivery of potassium salts are described, for example, in U.S. Pat. No. 3,538,214.

Alternatively, the potassium salt may be in the form of compressed granules coated with a semipermeable membrane material which penetrates the granules to form a honeycomb structure. Upon ingestion, gastrointestinal fluid dialyses into the compartments of the honeycomb structure and compartments within the honeycomb structure burst in a controlled manner as they become engorged with fluid to release the active agent in a substantially continuous manner. Suitable oral tablet honeycomb core structures and their preparation are described, for example, in U.S. Pat. No. 2,478,182. If desired, the magnesium salt may be present in the honeycomb core by admixing the magnesium and potassium salt to form the compressed granules which are coated, or a portion of and preferably all of the magnesium may be present in an overcoating which is applied to the surface of the honeycomb core to form a magnesium salt containing coating which erodes or dissolves upon ingestion thereby allowing the gastric fluid to imbibe the inner honeycomb core.

In a preferred embodiment, the potassium salt and optionally at least a portion of the magnesium salt is in the form of controlled release multiple-units formulation, containing per unit dose a multiplicity, typically in excess of 50, desirably at least 100, of individually coated or "microencapsulated" units of potassium salt in such a manner that the individual coated units will be made available in the gastrointestinal tract of the human host ingesting the formulation, as a tablet, capsule, sachet or the like. The release of bioavailable potassium, and optionally bioavailable magnesium, from such a controlled release multiple-unit form is generally controlled either by diffusion through a coating or by erosion of the coating by gastrointestinal fluid or a combination thereof. An advantage of the controlled release multiple-units dosage form is that high local concentrations of the potassium ingredient in the gastrointestinal tract is avoided due to the units being distributed freely throughout the gastrointestinal tract, generally independent of gastric emptying. Typically, the multiple-units formulation may be a capsule or sachet which disintegrates in the stomach to make available a multiplicity of individual coated units contained in the capsule, or a tablet which disintegrates in the stomach to make available a multiplicity of coated units originally combined in the tablet.

The magnesium salt, as indicated above, may either be present in the formulation as additional controlled release multiple-units, or in an uncontrolled, "instant" release form, or a combination thereof. In one subembodiment, the magnesium and potassium salts may be coated together as mixed crystals or pellets, having a size of between 0.1 to about 2 mm diameter.

In a preferred subembodiment, the bioavailable magnesium salt is released from the formulation at an average percent rate at least equal to the average percent rate of release of the potassium salt, based upon the total equivalent weight of magnesium and potassium respectively, in the unit dose formulation.

The equal to more rapid rate of release of magnesium insures that upon absorption of the same by the host, cell repletion of potassium is adequately enhanced, by virtue of concurrent magnesium cell repletion.

The individual units in the multiple-units formulation are prepared by coating the individual units with a substantially water-insoluble, but water-diffusible coating, such as a film coating, of a plastic or polymeric material which permits water diffusion. Examples of such materials include cellulose derivatives, for instance ethyl cellulose, acrylic polymers, vinyl polymers and other high molecular weight materials such as cellulose acetate, cellulose propionate, cellulose butyrate, cellulose valerate, cellulose acetate propionate, polyvinyl acetate, polyvinyl butyral, polymethyl methacrylate, polycarbonate, polystyrene, polyester, polybutadiene, ethylene-vinyl acetate copolymers and the like. The coating is generally applied to the unit crystal or pellet in the form of an organic or aqueous/organic solvent solution or dispersion of the plastic or polymeric material. Suitable organic solvents include, for example lower alkanols, such as ethanol or isopropanol, lower alkyl ketones, such as acetone, lower alkyl ethers, such as diethyl ether, or mixtures thereof. Hydrophobic adjuvants, to further retard or modify the release of the unit active agent, may also be employed as a liquid or solid dispersion in the organic solvent containing coating material. Suitable hydrophobic adjuvants include pharmaceutically inert hydrocarbons, and hydrocarbon derivatives, such as waxes, oils and fats and mixtures thereof. Preferred waxes include beef tallow, beeswax, solid paraffin, castor wax and higher fatty acids such as myristic, palmitic, stearic and behenic acids and the pharmaceutically acceptable waxy esters thereof. When employed, such waxy adjuvants may be present in the coatings in an amount between about 1% and about 25%, especially between about 3 and about 20%, by weight.

Preferably the coated units are of an average diameter between about 0.1 and 2 mm, preferably between about 0.2 and about 1.5 mm. The unit cores may be in the form of crystals or pellets. In the pellets, the core may be a combination of potassium salt, or a mixture of potassium and magnesium salts, and excipients. Suitable excipients include bulking agents, such as starch, microcrystalline cellulose and the like; binders such as cellulose derivatives such as methylcellulose, or hydroxypropylcelluloes, or polymeric binders such as polyethylene glycol, polyvinylpyrrolidone; or agar or gelatin. Generally such excipients are present in an amount between about 0.2 to about 25%. If desired, a buffer may be also employed to modify the core pH to between about 1 and about 7.5, preferably from about 4 to about 6. Suitable buffers include phosphoric acid salts, salts of citric or tartaric acid, salts of amino acids, and the like, in an amount between about 1 and about 30 percent by weight of the core. If desired, a plasticizer may also be added to the coating material, e.g. in an amount between about 0.01 to about one percent by weight, and include triacetin, acetylated monoglyceride, rape oil, olive oil, sesame oil, acetyltributylcitrate, acetyltriethylcitrate, glycerin, sorbitol, diethylmalate, diethyltartrate, polyethylene glycol and the like, and mixtures thereof. Inert fillers, pigments and other conventional excipients may also be present in minor amounts.

Generally the core crystals or pellets are coated in a fluidized bed or by pan coating and dried to remove the solvent. The amount of coating will be between about 1 to about 25% by weight, based on the weight of units, preferably between about 2 to about 20% by weight.

The units containing potassium salt in the form of coated crystals or pellets, may then be combined with magnesium salt, optionally also in the form of coated crystals or pellets, and placed within capsules, or sachets, containing a multiplicity of such units, or as tablets which disintegrate in the gastrointestinal tract to yield a multiplicity of such units.

The pharmaceutically acceptable adjuvants and excipients used in the preparation of disintegratable tablets are those conventionally used for this purpose. Suitable fillers include sugars, such as lactose, sucrose, dextrose and the like, calcium sulfate, calcium phosphates, starches such as rice starch, and microcrystalline cellulose. Useful binders include acacia, tragacanth, gelatin, starches, alginates, cellulose derivatives, and the like. Disintegrants include starches, clay, microcrystalline cellulose, gums, and starch derivatives. Lubricants include magnesium stearate, talc, colloidal silicon dioxide, and waxes.

The bioavailable magnesium active ingredient as indicated, supra, may be incorporated in the formulation as a controlled release ingredient, or may be incorporated into the formulation in a substantially non-controlled release manner, by simply mixing the bioavailable magnesium salt with the coated potassium salt and the tabletting excipients, and compressing the tablets by methods known, per se.

Methods for coating multiple unit crystals or pellets, including potassium chloride units, and the formation of capsules and tablets therefrom, is disclosed, for example, in U.S. Pat. No. 4,572,838, the disclosure of which is incorporated herein by reference.

In a preferred embodiment of the invention the solid oral composition contains, per unit dose, between 3 to about 15 milliequivalents bioavailable potassium and about 1 to about 7 milliequivalent bioavailable magnesium, and a milliequivalent ratio of potassium to magnesium between about 2:1 and about 14:1, preferably between about 2:1 and about 8:1, most preferably between about 2:1 and about 5:1.

In the following Examples, all parts are by weight unless otherwise indicated. The Examples are intended for illustrative purposes only and are not intended to limit the scope of the invention.

EXAMPLE 1

The following was performed in order to determine the effects of varying external magnesium concentration on the potassium conductance using, as a model, isolated guinea pig ventricular myocytes at various fixed concentrations of external potassium. At each level of potassium concentration, the concentration of magnesium which maximized potassium conductance was determined.

Guinea pig ventricular myocytes were isolated as follows. A male guinea pig was sacrificed by cervical dislocation and the heart was rapidly removed, rinsed and perfused with oxygenated calcium-free Tyrodes solution. The Tyrodes solution consists of 140 mM sodium chloride, 10 mM potassium chloride, 1 mM magnesium chloride, 10 mM glucose and 5 mM HEPES and the solution exhibits a pH of 7.26. The heart cells were dissociated by perfusion with an oxygenated, recycled collagenase solution, containing 0.02% collagenase (Sigma type IA), 0.1% bovine albumin, 20 $\mu$m calcium chloride in calcium free Tyrodes solution, for forty minutes. The atria were removed and ventricular myocytes were dispersed in a "KB" solution (70 mM potassium chloride, 3 mM dipotassium monohydrogen phosphate, 5 mM beta-hydroxybutric acid, 5 mM pyruvic acid, 20 mM taurine, 20 mM glucose, 5 mM magnesium sulfate, 5 mM succinic acid, 5 mM creative, 0.5 mM EGTA and 5 mM ATP, where the solution exhibits a pH of 7.3). Cellular debris was removed by filtration through a 200 um mesh screen and myocytes were incubated at room temperature for 1 hour. Cells were then placed in 30 ml of Tyrodes solution (140 mM sodium chloride, 10 mM potassium chloride, 1 mM magnesium chloride, 2 mM calcium chloride, 10 mM glucose and 5 mM HEPES exhibiting a pH of 7.4) at a temperature of 37° C., and recovered at 21° C. for one hour. A small number of cells are transferred to 35 mm culture dishes just prior to each experiment. The myocytes are bathed in a Tyrodes solution with the potassium modified to 4 and 7 mM (potassium chloride) respectively, without compensation for osmolality, in order to determine the optimum amount of serum magnesium needed to maximize potassium conductance within the normal expected range of serum potassium (4 to 7 mM).

Batch pipettes of 1-5 Mohm containing intracellular solution (125 mM potassium chloride, 4 mM magnesium chloride, 30 mM potassium hydroxide, 10 mM sodium chloride, 10 mM EGTA, 5 mM HEPES and 10 mM glucose at a pH of 7.2) were used to make giga-ohm seals with the cell membrane. An agar Ag/AgCl reference electrode was used to ground the bath. Voltage clamping was performed using a patch clamp amplifier.

Two protocols for voltage clamping were employed; either step voltage pulses of 0.8–5 sec., or a voltage ramp which ran at 6 mV per sec. No differences in the current voltage relationship were noted between the step or ramp protocols.

For a serum potassium concentration of 4 mM, the concentration of magnesium in mM needed to elicit maximum potassium conductance was found to be 0.9 mM divalent magnesium. This corresponds to a milliequivalent ratio of potassium to magnesium of 2:1. For a serum potassium concentration of 7 mM, the concentration of magnesium in mM needed to elicit maximum potassium conductance was found to be 0.26 mM divalent magnesium. This corresponds to a milliequivalent ratio of potassium to magnesium of 14:1.

Accordingly, for optimum muscle potassium conductance within the normal range of serum potassium levels, magnesium should be present in a milliequivalent ratio of potassium to magnesium between about 2:1 to about 14:1, based upon the aforementioned model.

EXAMPLE 2

Film coated potassium chloride granules having an average diameter of about 0.4–1.2 mm are prepared in accordance with Example 1 of U.S. Pat. No. 4,572,833 incorporated herein by reference. Such granules contain approximately 93% by weight potassium chloride, and are prepared by film coating potassium chloride crystals with a film-coating mixture containing paraffin, acetyl tributyl citrate, ethylcellulose, and silicon dioxide in isopropanol.

Film coated crystals of magnesium chloride hexahydrate are prepared as follows:

Approximately 1.0 kg of magnesium chloride hexahydrate is mixed with 5 g magnesium stearate and the mixture is screened through a number 12 screen. In 800 g of methylene chloride there is dissolved 20 g ethylcellulose, and 30 g polyvinylpyrrolidone and the solution sprayed onto the magnesium chloride hexahydrate while granulating the mixture in a Hobart mixer. The granulate is dried at a temperature of 40° C. and screened through a number 12 screen. The product contains 94.5% by weight magnesium chloride hexahydrate.

Magnesium aspartate hydrochloride is film coated in the same manner as magnesium chloride hexahydrate simply by substituting 1.0 kg magnesium aspartate hydrochloride trihydrate for the 1.0 kg magnesium chloride hexahydrate recited in the preceding paragraph. The film coated product contains about 94.5% by weight magnesium aspartate hydrochloride trihydrate.

EXAMPLE 3

A tablet composition containing 10 milliequivalent of potassium and 2 milliequivalents of magnesium wherein both are in controlled release form are prepared as follows:

To 804 parts by weight of the film coated potassium chloride of Example 2, there is added 214.8 parts by weight magnesium chloride hexahydrate coated granules of Example 2, 175 parts microcrystalline cellulose. 24 parts talc and 3.2 parts magnesium stearate and the mixture blended and compressed into tablets containing 10 milliequivalents potassium and 2 milliequivalents magnesium.

EXAMPLE 4

In the same manner as in Example 3, three formulations were prepared and tabletted. In compositions A and B there was employed uncoated magnesium aspartate hydrochloride trihydrate, and in composition C there was employed coated granules of magnesium aspartated hydrochloride trihydrate prepared according to Example 2 to provide controlled release of magnesium. In all three compositions, the coated potassium chloride granules employed were those of Example 2.

| Ingredient | Weight (mg) per tablet | | |
|---|---|---|---|
| | A | B | C |
| Coated KCl granules | 806 | 806 | 806 |
| Avicel PH 101* | 100 | — | 100 |
| Avicel PH 102* | — | 100 | — |
| Talcum | 50 | 50 | 50 |
| Mg Aspartate.HCl.3H$_2$O | 259 | 259 | — |
| Coated Mg Aspartate.HCl.3H$_2$O | — | — | 259 |
| Magnesium Stearate | 5.5 | 5.5 | 5.5 |
| Total Weight | 1220.5 | 1220.5 | 1220.5 |
| Tablet Thickness: | 8.3 mm | 8.3 mm | 8.3 mm |
| Tablet Hardness: | 12 | 12 | 12 |

*microcrystalline cellulose

The above tablets each contain approximately 10 milliequivalents potassium and 2 milliequivalents magnesium per tablet.

EXAMPLE 5

In the same manner as Example 3, tablets are prepared containing, per tablet, 203 mg coated magnesium chloride hexahydrate of Example 2, 644.8 mg coated potassium chloride of Example 2, 175 mg Avicel PH 101 microcrystalline cellulose, 24 mg talc and 3.2 mg magnesium stearate. The resulting tablets contained 8 milliequivalents of potassium and 2 milliequivalents magnesium per tablet, exhibited a hardness between 7–8 and a friability of 0.5% after about 4 minutes. The formulation was duplicated except that 188 mg Avicel PH 101 was employed per tablet and no magnesium stearate was used. The resulting tablets exhibited a hardness of 11 and a friability of 0.9% after 12 minutes.

EXAMPLE 6

In the same manner as Example 3 tablets are prepared containing, per tablet, 203 mg coated magnesium chloride hexahydrate of Example 2, 322.4 mg coated potassium chloride of Example 2, 100 mg Avicel PH 101 microcrystalline cellulose, 18 mg talc and 1.8 mg magnesium stearate. The tablets contain 4 milliequivalents of potassium and 2 milliequivalents magnesium per tablet.

What is claimed is:

1. A solid oral composition in the form of a tablet, capsule or sachet for the treatment or prophylaxis of potassium and magnesium deficiency in skeletal and cardiac muscle in a patient, said composition containing, as the active ingredients thereof,
   (a) about 3 to about 50 milliequivalents of bioavailable potassium in the form of a salt;
   (b) about 0.1 to about 25 milliequivalents of bioavailable magnesium in the form of a salt;
   (c) wherein the milliequivalent ratio of potassium to magnesium is between about 2:1 and about 14:1; and (d) wherein the potassium is in a controlled release form comprising said potassium and an overcoat layer comprising at least one polymer selected from cellulose, cellulose derivative, and acrylic containing or methacrylic containing polymers, adapted so that upon oral administration, the bioavailable potassium is released into the gastrointestinal tract at a rate sufficiently low so as to minimize potassium induced local gastrointestinal irritation.

2. A solid oral composition in the form of a tablet, capsule, or sachet for the treatment or prophylaxis of potassium and magnesium deficiency in skeletal and cardiac muscle in a patient, said comprising an active agent component consisting essentially of
  (a) about 3 to about 50 milliequivalents of bioavailable potassium in the form of a salt; and
  (b) about 0.1 to about 25 milliequivalents of bioavailable magnesium in the form of a salt; and
  a non-active component;
wherein the millequivalent ratio of potassium to magnesium is between about 2:1 and about 14:1; and wherein the potassium is in a controlled release form comprising said potassium comprising at least one polymer selected from cellulose, cellulose derivatives, and acrylic containing or methacrylic containing polymers adapted so that upon oral administration, the bioavailable potassium is released into the gastrointestinal tract at a rate sufficiently low so as to minimize potassium induced local gastrointestinal irritation.

3. A composition according to claim 1, wherein the potassium is in the form of potassium chloride.

4. A composition according to claim 1, wherein the magnesium is in the form of a pharmaceutically acceptable dietary supplement salt.

5. A composition according to claim 1, wherein the composition contains, per unit dose, between 3 to about 15 milliequivalent bioavailable potassium and about 1 to about 7 milliequivalent bioavailable magnesium, in a milliequivalent ratio of potassium to magnesium between about 2:1 and about 14:1.

6. A composition according to claim 5 in the form of a tablet.

7. A composition according to claim 5 wherein both the potassium and magnesium are each in the form of a bioavailable pharmaceutically acceptable salt.

8. A composition according to claim 7 wherein the potassium is in the form of potassium chloride.

9. A composition according to claim 8, in the form of a tablet.

* * * * *